(12) United States Patent
Heinlein et al.

(10) Patent No.: US 9,958,365 B2
(45) Date of Patent: May 1, 2018

(54) BIAXIAL MEASURING DEVICE AND METHOD FOR DETERMINING NORMAL AND SHEAR STRESS-CORRELATED MATERIAL PARAMETERS

(71) Applicant: Karlsruher Institut fuer Technologie, Karlsruhe (DE)

(72) Inventors: Kai Heinlein, Stuttgart (DE); Arnold Mager, Birkenfeld (DE); Rosemarie Wagner, Stuttgart (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 0 days. days.

(21) Appl. No.: 15/505,929

(22) PCT Filed: Jul. 24, 2015

(86) PCT No.: PCT/EP2015/001532
§ 371 (c)(1),
(2) Date: Feb. 23, 2017

(87) PCT Pub. No.: WO2016/029985
PCT Pub. Date: Mar. 3, 2016

(65) Prior Publication Data
US 2017/0268970 A1 Sep. 21, 2017

(30) Foreign Application Priority Data
Aug. 26, 2014 (DE) .................. 10 2014 112 161

(51) Int. Cl.
*G01N 3/08* (2006.01)
*G01N 3/06* (2006.01)
*G01N 3/24* (2006.01)

(52) U.S. Cl.
CPC .............. *G01N 3/068* (2013.01); *G01N 3/08* (2013.01); *G01N 3/24* (2013.01);
(Continued)

(58) Field of Classification Search
CPC ............ G01N 3/068; G01N 3/24; G01N 3/08; G01N 2203/0641; G01N 2203/0254; G01N 2203/0017; G01N 2203/0025
(Continued)

(56) References Cited

U.S. PATENT DOCUMENTS

| | | | | |
|---|---|---|---|---|
| 5,905,205 A | * | 5/1999 | Clay ........................ | G01N 3/08 73/819 |
| 6,247,370 B1 | * | 6/2001 | Ramaswamy ........... | G01N 3/08 73/798 |

(Continued)

FOREIGN PATENT DOCUMENTS

| | | |
|---|---|---|
| DE | 10305683 A1 | 10/2004 |
| DE | 102009020519 A1 | 11/2009 |

(Continued)

OTHER PUBLICATIONS

Quaglini V et al: "Experimental characterization of orthotropic technical textiles under uniaxial and biaxial loading", Composites Part A: Applied Science and Manufacturing, Elsevier Science Publishers B.V., Amsterdam, NL, vol. 39, Nr. 8, Aug. 1, 2008 (Aug. 1, 2008), pp. 1331-1342, XP023316709.

(Continued)

*Primary Examiner* — Jonathan Dunlap
(74) *Attorney, Agent, or Firm* — Leydig, Voit & Mayer, Ltd.

(57) ABSTRACT

A method for determining material parameters includes applying a character grid over a planar sample, clamping the planar sample in a frame in accordance with directions of orthotropy of the planar sample; collecting a first set of data that describes a first position of the character grid; applying predetermined normal and shear stresses to the planar sample thereby bringing the planar sample into a deformed state and changing the position of the character grid; collecting a second set of data that describes a second position (Continued)

of the character grid, determining a relative position change of the character grid by correlating the collected first set of data and the second set of data; determining a relative displacement and a current distortion state of the planar sample; determining a deformation equilibrium of the deformed state of the planar sample; and calculating the material parameters from the deformation equilibrium.

13 Claims, 4 Drawing Sheets (52) U.S. Cl.
CPC .......... *G01N 2203/0017* (2013.01); *G01N 2203/0025* (2013.01); *G01N 2203/0254* (2013.01); *G01N 2203/0282* (2013.01); *G01N 2203/0641* (2013.01)

(58) Field of Classification Search
USPC .......... 73/794–798, 800, 826, 828, 831–833, 73/838, 856–860
See application file for complete search history.

(56) References Cited

U.S. PATENT DOCUMENTS

| | | | |
|---|---|---|---|
| 6,487,902 B1 | 12/2002 | Ghosh | |
| 6,860,156 B1* | 3/2005 | Cavallaro | G01N 3/08 73/813 |
| 7,051,600 B1* | 5/2006 | Cavallaro | G01N 3/08 73/862.041 |
| 7,204,160 B1 | 4/2007 | Sadegh et al. | |
| 7,509,882 B2* | 3/2009 | Monteiro | G01N 3/08 73/862.046 |
| 7,762,146 B2* | 7/2010 | Brodland | G01N 3/04 73/826 |
| 7,785,517 B2* | 8/2010 | Poe | C08G 73/1067 248/576 |
| 7,836,778 B2* | 11/2010 | Kleinschnitz | B41F 15/36 73/159 |
| 8,061,214 B2* | 11/2011 | Liggett | G01N 3/08 73/788 |
| 8,082,802 B1* | 12/2011 | Sadegh | G01N 3/08 73/760 |
| 8,141,855 B2* | 3/2012 | McCracken | B29C 55/10 269/113 |
| 8,342,492 B2* | 1/2013 | Poe | F16F 15/04 248/200 |
| 8,641,408 B2* | 2/2014 | Collin | B29C 55/20 264/291 |
| 9,086,339 B2* | 7/2015 | Lee | G01R 31/2893 |
| 9,423,329 B2* | 8/2016 | Takeda | G01N 3/08 |
| 9,597,833 B2* | 3/2017 | Saha | B29C 55/12 |
| 9,746,401 B2* | 8/2017 | Kanade | G01N 3/02 |
| 2007/0180927 A1* | 8/2007 | Brodland | G01N 3/04 73/849 |
| 2008/0034885 A1* | 2/2008 | Monteiro | G01N 3/08 73/794 |
| 2009/0151468 A1* | 6/2009 | Kleinschnitz | B41F 15/36 73/826 |
| 2010/0162832 A1* | 7/2010 | Brauers | A61B 5/103 73/862.626 |
| 2011/0174056 A1 | 7/2011 | Liggett et al. | |
| 2011/0314926 A1* | 12/2011 | Hanabusa | G01N 3/04 73/826 |
| 2015/0101418 A1* | 4/2015 | Campbell | G01N 3/08 73/826 |
| 2015/0253227 A1* | 9/2015 | Takeda | G01N 3/08 73/788 |
| 2015/0377754 A1* | 12/2015 | Kanade | G01N 3/068 73/788 |

FOREIGN PATENT DOCUMENTS

| | | |
|---|---|---|
| DE | 102012219593 A1 | 4/2013 |
| EP | 2570791 A2 | 3/2013 |
| WO | WO 2012100780 A1 | 8/2012 |
| WO | WO 2014115130 A2 | 7/2014 |

OTHER PUBLICATIONS

B. Bridgens et al: "Inter-laboratory comparison of biaxial tests for architectural textiles", The Journal of the Textile Institute, vol. 103, Nr. 7, Jul. 1, 2012 (Jul. 1, 2012), pp. 706-718, XP055225831.

* cited by examiner

BIAXIAL MEASURING DEVICE AND METHOD FOR DETERMINING NORMAL AND SHEAR STRESS-CORRELATED MATERIAL PARAMETERS

CROSS REFERENCE TO RELATED APPLICATIONS

This application is a U.S. National Stage Application under 35 U.S.C. § 371 of International Application No. PCT/EP2015/001532 filed on Jul. 24, 2015, and claims benefit to German Patent Application No. DE 10 2014 112 161.9 filed on Aug. 26, 2014. The International Application was published in German on Mar. 3, 2016 as WO 2016/029985 A1 under PCT Article 21(2).

FIELD

The invention relates to a biaxial measuring device and to a method for determining normal stress- and shear stress-correlated material parameters. The invention further relates to a suspension device for a planar sample in the measuring device and to a measurement assembly consisting of said measuring device and the sample.

BACKGROUND

Devices for detecting material parameters in flexible and planar components in stressed or distorted states are known from the prior art. Material parameters are parameters that provide information on the linear-elastic deformation of a component, inter alia, e.g. the shear modulus as a material constant or the modulus of elasticity as a relationship between stress and distortion when a solid body is deformed and linear elastic behavior. To determine various material parameters, normal and shear stresses can be applied to planar samples. The material parameters can be calculated from the measured data using known material laws. According to the orthotropic material law, the material parameters are independent of one another, the moduli of elasticity and the transverse strain in the direction of orthotropy being independent of the shear modulus for an even stress state and an even distortion state. Previously, determining the material parameters required three differently designed tests, the determination of the transverse strain being limited to the linear material behavior. Therefore, normal stresses always have to be superposed to calculate the shear modulus.

For flexible materials, shear tests for determining the shear modulus require prestress in the direction of orthotropy to prevent the formation of creases in the material sample upon shear loading. Generally, what are known as shear frames are used, in which the sample is mounted in a prestressed manner and the square shear frame is pulled via the diagonals. The amount of prestress determines the deformation behavior, i.e. the greater the prestress, the smaller the shear distortions. The displacements of the sample can be measured by means of travel sensors or optical measurement methods.

Using this method, the material parameters can only be determined for linear stress-strain behavior. As soon as the behavior stops being linear, the material parameters can no longer be determined, or can only be determined with very low precision.

DE 10 2009 020 519 A1 describes a device for testing various parameters of high-strength flexible textile laminate materials. Biaxial loads are applied to a sample, with a view to measuring a force at which the material fails.

EP 2 570 791 A1 discloses a device for determining the biaxial strain parameters of a sample. The sample is cross-shaped and stress is applied to each of the four arms of the sample. A frame is constructed from frame parts that can move relative to one another and in which a fixed and a movable member are both associated with a tensile test machine.

U.S. Pat. No. 7,204,160 B1 describes a device by which any stress state can be applied to a cross-shaped, planar sample by means of a cylindrical test apparatus. In flexible samples having high transverse strain, the surface of the sample is bent twice. Since the influence of the double bend of the surface on the material parameters is unknown, the additional bend components cannot be calculated therefrom.

WO 2012/100 780 A1 also discloses an S-shaped biaxial measuring device, constructed from two fork supports for applying tensile stress, and two curved arms. The curved arms have a plurality of sample mounts that hold a sample arranged in the center.

To determine the transverse strain, the stress-strain behavior has to be linear. However, for non-linear material behavior, as is the case in particular with large distortions, i.e. of greater than 10%, there is no basis for separating the geometric non-linear components from the elastic components, especially in the case of a shear load.

The orthotropic material law for loads in the direction of orthotropy is based on the normal distortions being independent of the shear distortions. In flexible materials, crease-free shear loading is only possible if a normal stress state is superposed thereon. For composite materials having shear resistance, the moduli of elasticity have to be determined by breaking down the stress components in the filament direction when the load is not parallel thereto, i.e. the load is not applied in a (main) fiber direction of the composite material. For materials having low shear resistance, a non-parallel load of this kind leads to internal twisting, and known material laws, in particular for composite materials, are only applicable to a limited extent. The material parameters can then only be determined to an insufficient extent or for small distortions (in which the behavior is still linear).

SUMMARY

In an embodiment, the present invention provides a method for determining normal stress- and shear stress-correlated material parameters using a biaxial measuring device comprising a frame for clamping a planar sample of a bendable and flexible material, a plurality of drives for applying normal and shear stresses to the sample, and an optical measuring apparatus operatively coupled to a data processing unit. The method includes a) applying a predefined character grid over the planar sample, wherein an orientation of the character grid is either irregular or correlates with directions of orthotropy of the planar sample, and clamping the planar sample in the frame in accordance with the directions of orthotropy of the planar sample, b) collecting, by the optical measuring apparatus, a first set of data that describes a first position of the character grid and sending the collected first set of data to the data processing unit, c) applying, simultaneously, predetermined normal and shear stresses to the planar sample by the plurality of drives, thereby bringing the planar sample into a deformed state and changing the position of the character grid, d) collecting, by the optical measuring apparatus, a second set of data that describes a second position of the character grid and sending the collected second set of data to the data processing unit, e) determining a relative position change of the character grid by correlating the collected first set of data and the second set of data and determining therefrom, by the data processing unit, a relative displacement and a current distortion state of the planar sample, f) determining, from the relative displacement and the current distortion state of the planar sample, a deformation equilibrium of the deformed state of the planar sample, wherein the deformation equilibrium correlates with the material parameters, and g) calculating the material parameters from the deformation equilibrium and outputting the material parameters.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

In an embodiment, the present invention provides a method for determining normal stress- and shear stress-correlated material parameters, by which the material parameters can also be determined in non-linear distortions ranges by means of the measured distortions.

A suspension device is described herein for suspending a sample firmly and securely such that the sample can be clamped in the measuring device without any creases.

A measurement assembly is described herein for measuring bendable and flexible materials in the range of non-linear distortions.

A method according to an embodiment of the invention for determining normal stress- and shear stress-correlated material parameters uses a biaxial measuring device comprising a frame for clamping a planar sample of a bendable and flexible material, and a plurality of drives for applying shear stresses and shear strains to the sample. The biaxial measuring device further comprises an optical measuring apparatus operatively coupled to a data processing unit.

In a first step a), the method comprises applying a predefined character grid over the planar sample, the orientation of which grid either correlates with the directions of orthotropy of the sample at regular distances, or is irregular. The sample is clamped in the frame in accordance with the directions of orthotropy of said sample. In linear elasticity theory, the orthotropy can be defined as a special case of anisotropy in which the stiffness or flexibility matrix has a particularly simple shape (nine constants instead of 21 constants as in general).

In a following step b), a first set of data that describes the first position of the character grid is collected by means of the optical measuring apparatus, and the collected set of data is sent to the data processing unit. Afterwards, predetermined normal and shear stresses are applied to the sample by means of the plurality of drives, thereby bringing the sample into a deformed state and changing the position of the character grid in a stop c).

In step d), a second set of data that describes the second position of the character grid is recorded by means of the optical measuring apparatus, and the second set of data is sent to the data processing unit. Next, a relative position change of the character grid is determined by correlating the collected first and second sets of data in a step e).

Distortions and a current strain state of the sample are determined therefrom by means of the data processing unit. In a step f), a deformation equilibrium of the deformed state of the sample is determined from the displacement and the current distortion state of the sample, the deformation equilibrium correlating with the material parameters. Next, the material parameters are calculated from the deformation equilibrium and output in a step g).

By means of a method according to an embodiment of the invention, moduli of elasticity, transverse strain and the shear modulus of the material being tested can be determined for one sample and in one test. The determination of the material parameters applies to load in the direction of orthotropy and to loads below 45° for non-linear behavior and any distortions.

Prestress to be applied can be within a range between 0 kN/m and 100 kN/m, the upper limit merely indicating the maximum stress to be applied at that time by the measuring apparatus and not being limited by the numerical value. For the moduli of elasticity, the material parameters can, for example, be between 100 kN/m and 1000 kN/m for films and from 500 kN/m to 5000 kN/m for coated fabrics, in relation to the thickness of the samples. Nevertheless, material parameters having lower or even higher moduli of elasticity can also be measured.

According to embodiments of the invention, steps b) to f) of the aforementioned method sequence can preferably be repeatedly carried out, the normal and shear stress to be applied being varied, i.e. increased or decreased, with each repetition. This variation can take place gradually or in 'load steps,' it being possible to reach a constant distortion rate by constantly increasing the stress by a particular value.

In a preferred embodiment of the analysis, the material parameters can be calculated as follows:

In order to determine the first or second position of the character grid, distances between three predetermined points on the character grid can be detected, it being possible to join the points on the character grid by (imaginary) lines and to determine an angle between the lines of the points on the character grid and a predetermined x- and y-axis of the measuring device. The distances and the angles form a set of data that can be processed further.

An x-axis or y-axis can be predetermined by the measuring device or the frame and the measurement technique, or can be self-defined. By means of the optical measuring apparatus, points on the character grid can be determined and the position thereof in the x-direction and y-direction can be calculated, it being possible to use the exact geometric conditions of the sample.

Thus, the displacement of the character grid over the sample can be measured and the change in the distances between adjacent points is converted into the distortions by means of the following functional relationships. The initial values are the measured distances between the points $P_1$ and $P_2$ and the points $P_1$ and $P_3$ on the character grid, which are in any given position relative to one another and form the angles $\alpha_x$ and $\alpha_y$ of the distances to a predetermined x- and y-axis of the frame. These distances can be converted into orthogonal components $a_x$ and $a_y$ using the known x- and y-directions and correspond to the distances in the x- and y-direction between each set of two points ($P_1$ to $P_2$ and $P_1$ to $P_3$). In each loading step, the displacement of the character points on the character grid in the x- and y-direction is measured, after which distortions or distortion parameters $\epsilon_{11}$, $\epsilon_{22}$ and $\gamma_{12}$ can be determined for any displacements using the differences between the displacements ($u_2$, $u_3$ displacement of points $P_2$ and $P_3$ in the x-direction and $v_2$, $v_3$ displacement of points $P_2$ and $P_3$ accordingly in the y-direction):

$$\varepsilon_{11} = \frac{1}{a_x}\sqrt{(a_x + u_2 - u_1)^2 + (v_2 - v_1)^2} - 1$$

$$\varepsilon_{22} = \frac{1}{a_y}\sqrt{(a_y + v_3 - v_2)^2 + (u_3 - u_2)^2} - 1$$

$$\alpha_x = \arctan\frac{v_2 - v_1}{a_x + u_2 - u_1}$$

$$\alpha_y = \arctan\frac{u_3 - u_2}{a_y + v_3 - v_2}$$

$$\gamma_{12} = \alpha_x + \alpha_y$$

From the aforementioned distortions and the lengths $a_x$ and $a_y$ (which may be unstrained or already pre-strained), strained lengths $a_1$ and $a_2$ can be calculated:

$$a_1 = a_x \cdot (1 + \epsilon_{11})$$

$$a_2 = a_y \cdot (1 + \epsilon_{22})$$

Next, applied shear stresses $\tau_{xy}$, and normal stresses $\sigma_{xx}$, $\sigma_{xy}$ can be used to determine the stresses within the material, it being possible to apply a stress state that is constant for the directions of orthotropy in a measurement field (which can be determined by the sample size). This thus defines a deformation equilibrium that correlates with the material parameters. Owing to the prestress in the sample for preventing creases in the normal and shear tests and since normal stresses are affecting the shear distortion, components of the geometric rigidity can be subtracted in order to determine the shear modulus as purely a material parameter, without taking account of an influence from the stiffening effect of the prestress. For this approach, an equilibrium in the deformed state is determined in relation to the current distortion state (also referred to as deformation equilibrium). The special feature here is that the directions of orthotropy also rotate in flexible materials and the stresses act in the direction of the rotated axes of orthotropy in the deformed state.

To calculate the material parameters in the deformed state, the following functional relationships can also be used:

$$\sigma_{11} = \frac{a_y}{a_2} \cdot \frac{\sigma_{xx} \cdot \cos\alpha_y - \tau_{xy} \cdot \sin\alpha_y}{\cos\gamma_{12}}$$

$$\sigma_{22} = \frac{a_x}{a_1} \cdot \frac{\sigma_{yy} \cdot \cos\alpha_x - \tau_{xy} \cdot \sin\alpha_x}{\cos\gamma_{12}}$$

$$\tau_{12} = \frac{a_y}{a_2} \cdot \frac{-\sigma_{xx} \cdot \sin\alpha_x - \tau_{xy} \cdot \cos\alpha_x}{2\cos\gamma_{12}} + \frac{a_x}{a_1} \cdot \frac{-\sigma_{yy} \cdot \sin\alpha_y - \tau_{xy} \cdot \cos\alpha_y}{2\cos\gamma_{12}}$$

-continued $$\alpha_x = \arctan\left(\frac{\sigma_{xx} \cdot a_x \cdot a_2 \cdot \sin\gamma_{12} - \tau_{xy} \cdot (a_x \cdot a_2 \cdot \cos\gamma_{12} - a_y \cdot a_1)}{\sigma_{xx} \cdot a_y \cdot a_1 + \sigma_{yy} \cdot a_x \cdot a_2 \cdot \cos\gamma_{12} + \tau_{xy} \cdot a_x \cdot a_2 \cdot \sin\gamma_{12}}\right).$$

Thus, for the deformation equilibrium of the material in the deformed state, the following relationship can now be established in relation to the directions of orthotropy for an even distortion state. The as yet unknown material parameters (here denoted by $E_{1111}$, $E_{2222}$, $E_{1122}$, $E_{2211}$ and $E_{1212}$) can be calculated from said relationship, wherein $E_{1122} = E_{2211}$ for reasons of symmetry:

$$\begin{bmatrix} \sigma_{11} \\ \sigma_{22} \\ \tau_{12} \end{bmatrix} = \begin{bmatrix} E_{1111} & E_{1122} & 0 \\ E_{1122} & E_{2222} & 0 \\ 0 & 0 & E_{1212} \end{bmatrix} \cdot \begin{bmatrix} \varepsilon_{11} \\ \varepsilon_{22} \\ \gamma_{12} \end{bmatrix}.$$

As a result, to calculate 15 variables there are also 15 equations available, said variables being three distortions of the material in the deformed state $\epsilon_{11}$, $\epsilon_{22}$, $\gamma_{12}$, three stresses in the deformation equilibrium $\sigma_{11}$, $\sigma_{22}$, $\tau_{12}$, the strained lengths $a_1$, $a_2$, two angles of the rotated lengths $\alpha_x$, $\alpha_y$, and the unknown material parameters $E_{1111}$, $E_{2222}$, $E_{1122}$, $E_{2211}$ and $E_{1212}$.

As described above, the stresses and the geometric variables for each loading can be calculated from the applied forces and measured displacements or applied displacements and measured forces. In each load step, therefore, the four material parameters can be determined for any stress state. The described analysis method makes it possible to use stresses and distortions to determine the material parameters, the exact geometric conditions being applied for converting the measured displacement into the distortions.

In an alternative method sequence, a test of this kind can be carried out in two steps, the sample being clamped in the test apparatus in the direction of the directions of orthotropy, strained to a predetermined value and then made rhomboid. Making the sample rhomboid produces the above geometric determination equations, which make it possible to calculate the moduli of elasticity and the transverse strain from the measured or applied variables, even without any shear resistance. Advantageously, it is thus possible to test materials that have no shear resistance or only very low shear resistance and high levels of twist in the directions of orthotropy, materials that have no transverse strain or only very low transverse strain or high levels of twist, and even materials having a certain level of transverse strain and shear resistance.

In the process, the material parameters can be clearly and unambiguously separated when normal and shear stress states and large distortions of geometrically non-linear influences are applied simultaneously.

The normal and shear stresses applied simultaneously in step c) for deforming the sample can be in the non-linear range, non-linear ranges being taken to means angular twisting of in particular greater than 10°. Within the meaning of the invention, non-linear can mean that the stress-strain curve of which the tangent corresponds to the modulus of elasticity has a curve shape other than a linear curve. This occurs in particular when the difference between the secant modulus and the actual modulus of elasticity becomes greater than 10%.

A biaxial measuring device for use in the method for determining normal stress- and shear stress-correlated material parameters comprises a frame for clamping a planar sample of a bendable and flexible material, and a plurality of drives for applying stresses to the clamped sample. The biaxial measuring device is associated with an optical measuring apparatus operatively coupled to a data processing unit. By way of the drives, predetermined normal and shear stresses can be simultaneously applied to the clamped sample in the normal and parallel direction with respect to the directions of orthotropy.

In particular, it is advantageous for normal and shear stress states to be able to be applied to the sample simultaneously. This then means that only one test is required, instead of three separate tests previously. This can save time and costs, while also producing higher quality results. In addition to making the sample a symmetrical rhombus, it is also possible to produce asymmetrical distortion states. Any symmetries and any quadrilaterals can be made from the substantially square sample. Until now, this was not possible in the prior art, especially in shear tests.

The device frame can be constructed from a plurality of profiles, and can be closed or open. Preferably, the frame can have a square basic shape, it also being possible to construct frame parts from rectangular profiles. Other shapes, e.g. hexagonal frames, are also possible.

There can also be at least eight drives. Two or more drives can be arranged along one side edge of the frame. In the process, one or more of the at least two drives can be intended for producing normal stress and at least one other drive can be intended for generating a shear stress.

To apply a uniform normal or shear stress to the sample in a predetermined direction of orthotropy, two or more drives can be provided and can be arranged on sides of the frame that face away from one another. The sample can thus be uniformly pulled and made correspondingly rhomboid. The number of drives and the sample mounting are advantageously separate, meaning that an unimpeded deformation state of the sample can be achieved when there are only eight drives.

Using the drives arranged as described herein, it is possible to introduce any stress state into the sample by two drives preferably acting normally on the edges of the samples and two drives at each opposite corner of the sample bringing about the rhomboid shape of the sample.

Furthermore, a rail can be arranged within the frame, in which rail an edge portion of the sample can be mounted so as to be linearly displaceable. As a result of the distortion of the sample caused when a corresponding stress is applied, the drives can move along the rail and maintain uniform distortion.

The measuring device can also comprise a suspension device having a plurality of carriages that can be connected to the edge portion of the sample. Desired prestress can then be applied to the sample in a reliable and durable manner.

By attaching the sample to rails that allow the sample edges to be displaced in parallel with the edges, it is possible to dispense with complex production of cross-shaped samples having additional tabs, which are required to allow for unimpeded transverse strain.

The optical measuring apparatus can also comprise one or more optical sensors for detecting the character grid of the sample. The sample distortion can thus be measured in a contactless manner.

The measuring device can comprise one or more control devices which can be coupled to the plurality of drives so as to control them in an open- and closed-loop manner, the control unit(s) being operatively coupled to the data processing unit. The distortion of the sample can thus be adjusted gradually and in a simple manner. In the process, three deformation variants of the sample can be achieved. In the case of travel-based deformation, with constant displacement path and simultaneous measurement of force, a predefined speed in mm/min is produced, it being possible for the measurement signal being detected to be a path that the drives are to cover. In the case of force-based deformation, the forces in the x- and y-direction can be predefined separately and the force from the force sensors can be used as the measurement signal. Preferably, the deformation variant "real-time-based" can also be selected, a recorded displacement being determined on the basis of the sample deformation. This implies constant sample deformation in one direction in each case. Control can be carried out by analyzing the optical measurement results. The measurement signal thus signifies a path or the distortion of the sample on the basis of the analysis of the optical measurement.

One or more suspension devices can be provided in a measuring device for one planar sample, as described above. The suspension device comprises three or more carriages that can be connected to an edge portion of the sample. Two or more of the three of more carriages can be movably mounted on a runner rail. Furthermore, one or more of the carriages are rigidly and immovably connected to the runner rail. Preferably, three suspension devices can be provided on each side such that each drive has a suspension device. For example, there are preferably two suspension devices for normal stresses and one suspension device for generating shear stress on the sample.

The suspension device is connected to the drives by means of pulling elements acting as connecting apparatuses. These elements can be cables, wires, threaded rods or bars. A suitable pulling element can be selected according to the application and the stress to be applied.

Advantageously, cross-shaped samples having special tabs for suspension no longer have to be produced. Simple, planar sample pieces can be used, thus reducing production costs for the sample.

The suspension device can hold a beading, around which an edge portion of the sample can be placed, it being possible to undetachably connect the beading to an attachment portion of the sample. In this case, the attachment portion can in particular be welded, bonded or stitched. The beading can be a cable, a flexible or rigid bar, or a rod. The suspension device can comprise three or more beading profile blocks each having a recess in which at least portions of the coverable beading can be received. At the same time, the beading profile blocks can be connected to the at least three carriages. The sample can thus be mounted in a simple manner and does not require its own separate tabs or the like. The suspension device requires high rigidity and allows the tensile stress to be distributed uniformly over the sample.

A measurement assembly can comprise a measuring device, as described above, and a planar sample of a bendable and flexible material. In this case, the sample that can be mounted in the measuring device preferably has a planar geometry. In addition, the sample can comprise a character grid predefined on its surface for optically detecting distortions as a result of applicable normal and shear stresses from optically detectable points.

Points can preferably be provided for the character grid since they have well-defined dimensions and are thus more easily detectable by the optical measuring apparatus. In general, other simple geometric shapes are also possible, such as crosses, squares or triangles. The character grid itself can have a symmetrical or regular design, i.e. be formed from points equidistant from one another, and can for example correlate with the directions of orthotropy of the sample. In addition, the character grid can also be applied in any manner regardless of symmetry of the sample.

A device according to embodiments of the invention is based in particular on a measuring device for determining normal stress- and shear stress-correlated material parameters of flexible and bendable materials.

Figure 1:
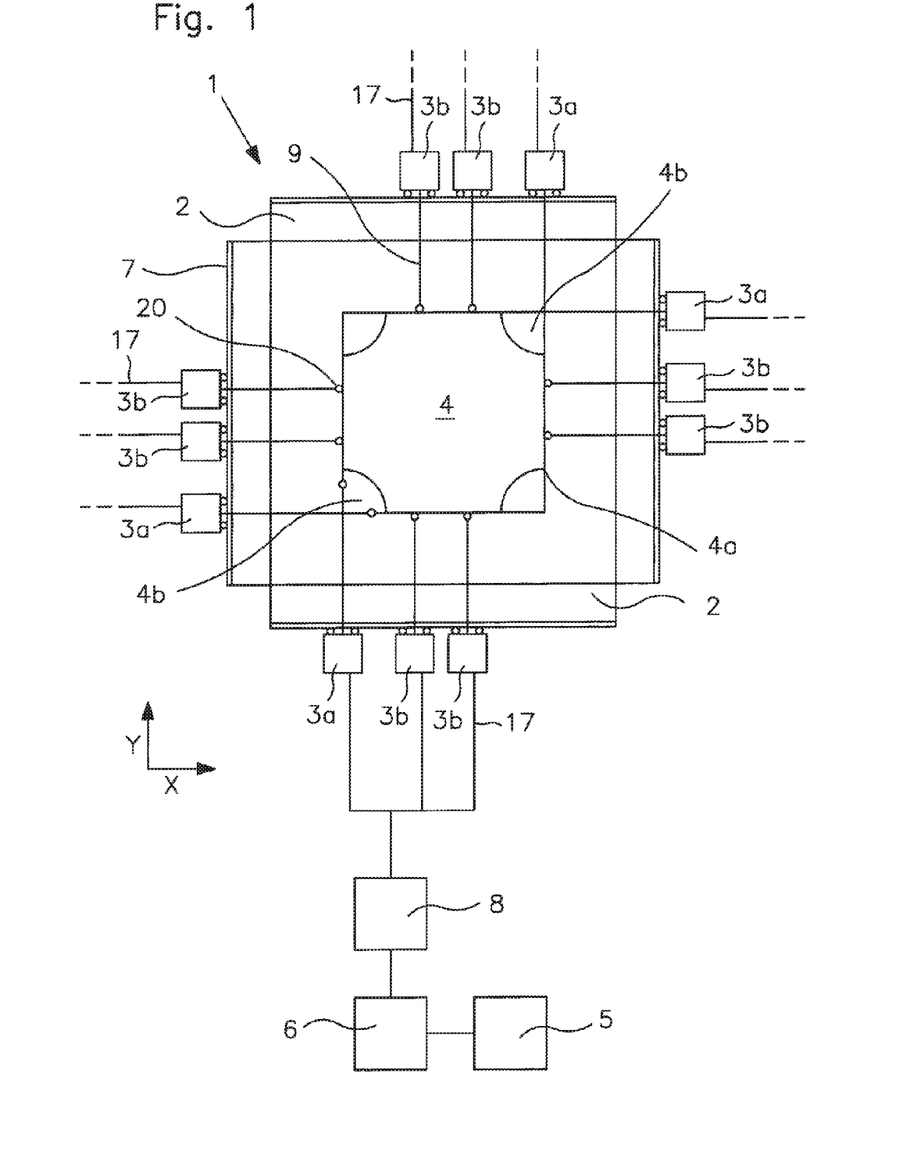
FIG. 1 is a schematic view of a measuring device according to an embodiment of the invention containing a non-loaded sample.

FIG. 1 shows a measuring device 1 according to an embodiment of the invention comprising a square frame 2 consisting of substantially four linear frame parts. On each frame part, rails 7 are arranged on the outside of the frame 2. Drives 3a, 3b are provided and engage in the rails 7 by means of connection devices 9, in this case cables acting as pulling elements or other pulling or pushing devices such as bars or rods, or a clamping suspension device. In turn, the suspension device has a guide or runner rail (see FIG. 3) connected to a sample 4. The sample 4 is substantially planar and square. In FIG. 1, the sample 4 is shown in a clamped but still unloaded state.

The frame parts of the frame 2 can be constructed from two rectangular hollow profiles arranged one above the other. It is necessary for the frame parts to be in two parts so that the drives 3a, 3b can be arranged so as to have their longitudinal axes on the middle surface of the square sample 4 to prevent the sample rotating out of the sample plane. The ideal (sample) plane in which the sample should be during measurement is defined by the plane formed by the axes of the drives. In this case, the frame 2 is of such a size that the sample 4 can be made rhomboid by 45°. In FIG. 1, three drives 3a, 3b are arranged along each of the four sides of the frame 2.

The drives 3a, 3b are divided into different types of drives, two of the three drives being in each case spindle drives 3b specifically for normal loading, for example. The third drive is for example a spindle drive 3a for generating a shear load on the sample 4. This can also be seen from the connection devices 9 by which the spindle drives 3b each act in a central portion of a side edge 4a for the shear loading. The spindle drives 3a, intended to produce shear loading, are attached at two corner portions 4b of the sample 4. The spindle drives 3a, 3b are mounted on the frame 2 so to be displaceable in parallel with the frame parts or profiles, and can rotate about a z-axis.

Furthermore, all the drives 3a, 3b are connected, by means of electrical connections 17, to a measurement and control unit 8 that controls the drives 3a, 3b in an open- and closed-loop manner. To see this more clearly, example connections 17 between the components are shown in a lower region of FIG. 1; the connections 17 or the portions thereof to the left, right and above the frame 2 are only shown in dashed lines in FIG. 1. Said connections are also operatively coupled to the measurement and control unit 8. Separate measurement and control units can also be provided for each spindle drive 3a, 3b. It is also possible to divide the units into measurement and control units for separately monitoring the shear stress and shear strain.

In addition, the measuring device 1 comprises a data processing unit 6, which can be a standard PC or can be connected to one. An optical measuring device 5 (shown schematically in FIG. 1) is also operatively connected to the data processing unit 6. The sample 4 can comprise a character grid, preferably a point grid, used for optical detection. So that this character grid can be optically detected, the optical measuring device 5 is in particular an optical sensor arranged above the measuring device 1 or above the sample 4 at a suitable height. Depending on the design of the measuring device 1, the optical sensor 5 can also be arranged below the sample. In this case, 'below' means below a surface of the sample extending in the x-y direction. In this case, an x-y orientation is predetermined by the geometry of the frame 2. The zero point is selected in a corner, for example a left-hand bottom corner of the frame 2.

Figure 2:
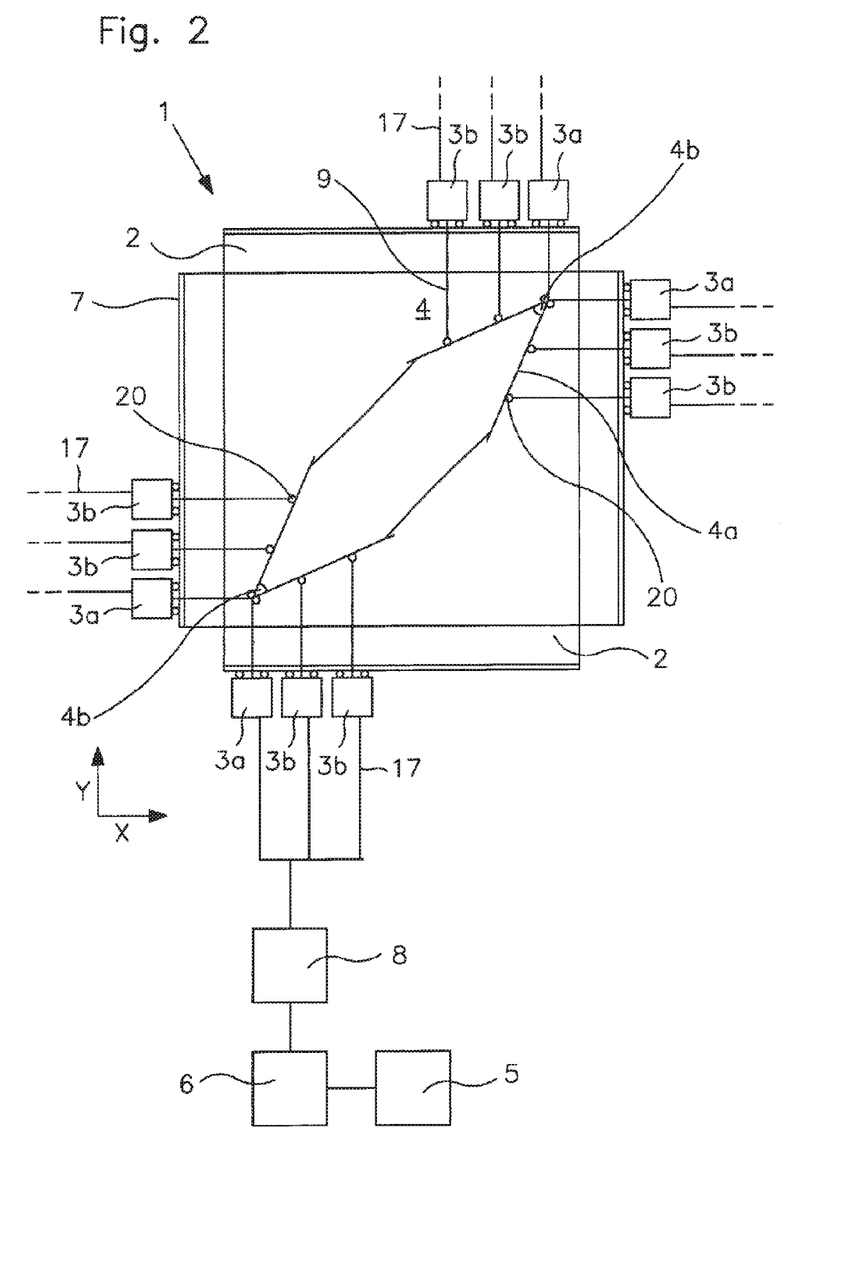
FIG. 2 is a schematic view of a measuring device according to an embodiment of the invention having a clamped sample in a loaded state.

FIG. 2 shows the same device 1, the spindle drives 3a, 3b now having been driven such that they have each generated a shear stress or shear strain on the sample 4. In the process, the pulling elements of the connection device 9 shorten and the spindle drives 3a, 3b move along the rails. The square sample 4 is made rhomboid as the stress increases. In this case, the dimensions of the frame 2 are selected such that a sample having corresponding dimensions of approximately 60 cm×60 cm is made rhomboid by up to 45°.

Figure 3:
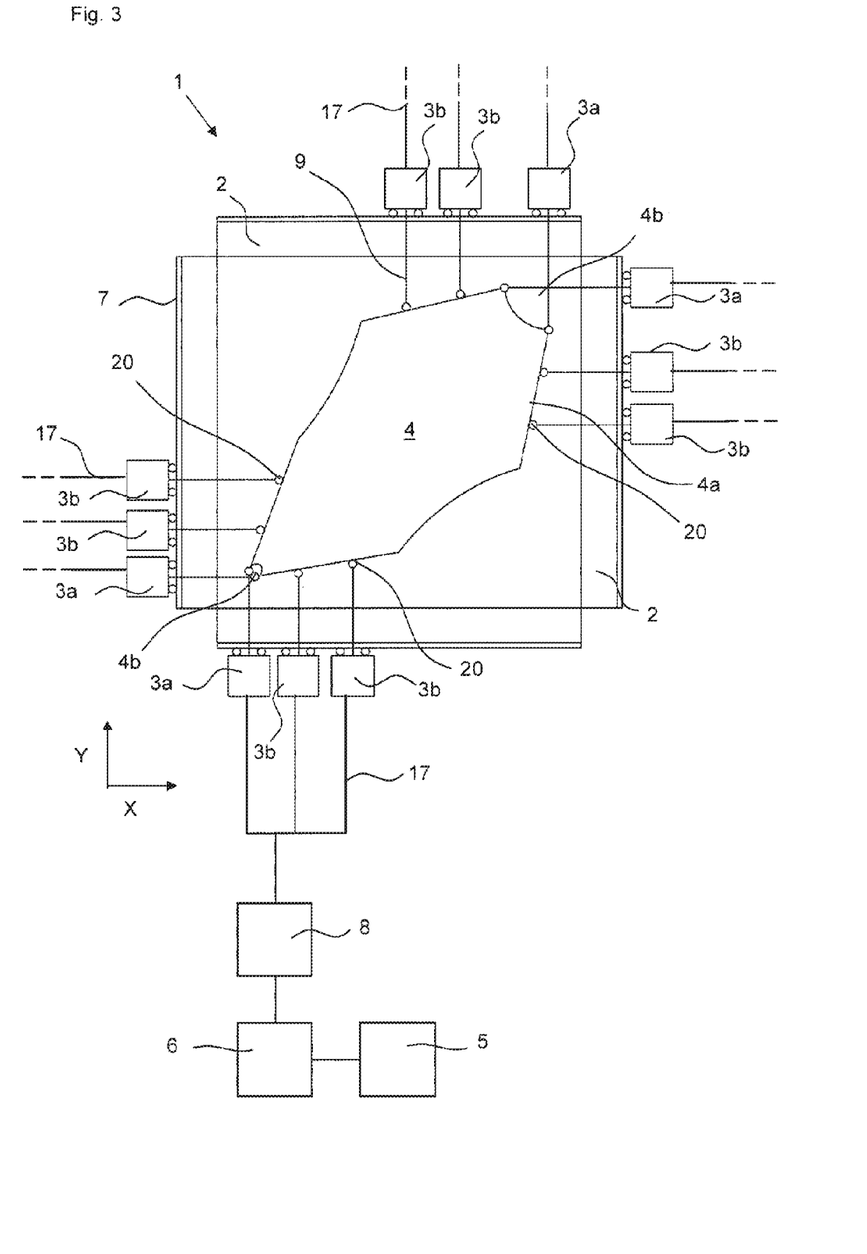
FIG. 3 is a schematic view of a measuring device according to an embodiment of the invention having a clamped sample in another loaded state.

FIG. 3 shows the same measuring device 1 as in the preceding figures, but the spindle drives 3a, 3b have now been driven such that the square sample 4 is not made symmetrically rhomboid in this case, but rather is stressed asymmetrically. In this case, a first region (left-hand bottom corner of the frame 2 in FIG. 3) is made more rhomboid than a second region (right-hand upper corner of the frame 2 in FIG. 3). As a result, different size stresses that could not be produced in the laboratory before now can now be applied to the sample 4.

Figure 4:
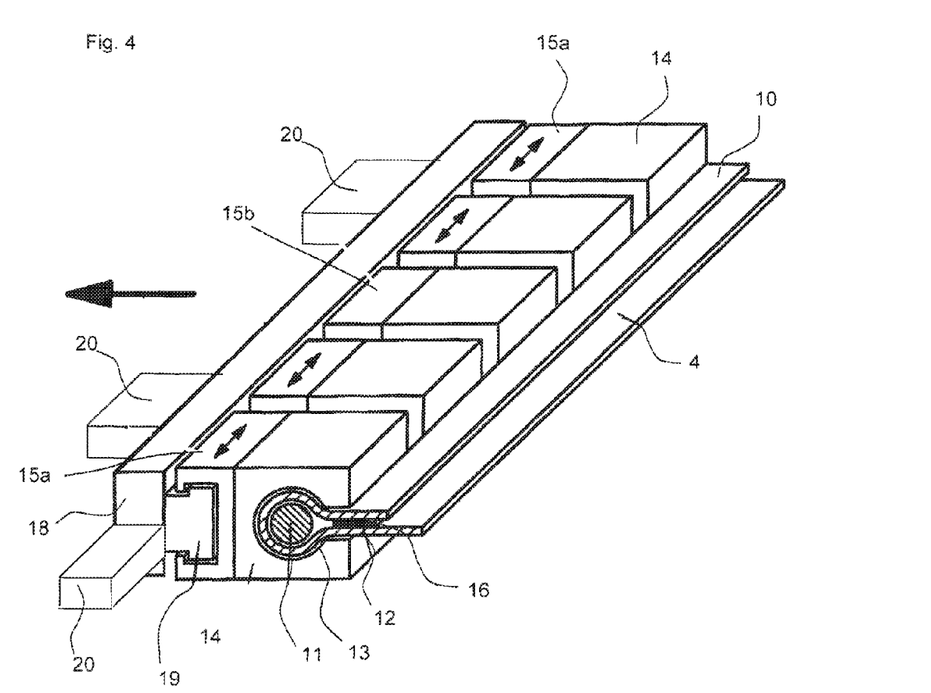
FIG. 4 is a view of a detail of a suspension device according to an embodiment of the invention.

To rigidly suspend the sample 4, or specifically to produce stresses in the non-linear range as in this case, it is necessary to have a special suspension. In this regard, FIG. 4 shows a view of a detail of a suspension device that can be attached to edges of the sample 4. One suspension device is provided in each case, and acts on an edge portion 10 of the sample 4 in a particular way.

The edge portion 10 of the sample in FIG. 4 is placed around a beading 11 and overlaps an attachment portion 12 of the sample 4. The edge portion 10 and the attachment portion 12 are rigidly interconnected by means of an attachment seam or weld seam 16. The beading 11 enclosed by a part of the sample 4 is received in five beading profile blocks 14. For this purpose, the beading profile blocks 14 comprise suitable recesses 13. The shape of these recesses 13 corresponds at least to the diameter of the beading 11 plus double the thickness of the sample 4. The sample is thus fixed in position and securely held. The beading profile blocks 14 are also rigidly connected to carriages 15a, 15b mounted on a runner rail 19. On the suspension device, a central carriage 15b is rigidly connected to the runner rail 19, the four other carriages 15a being movably mounted on the runner rail 19 to the left and right of the central carriage 15b. The runner rail 19 is mounted on a mount 18 that holds the runner rail 19 in position. The mount 18 is also rigidly connected to a connection device 20, the connection device 20 being arranged on the mount 18 so as to be in direct extension in relation to the fixed carriage 15b and connecting to the connection device 9 of the respective drives 3a, 3b.

A black arrow toward the left-hand side of FIG. 4 illustrates that this force is a pulling force to be applied in this direction. The advantage of this type of suspension is in particular that a pulling force can be transmitted to the sample 4 without having to establish another transverse connection. The sample 4 is prevented from sliding in the pulling direction, and thus the pulling force is maintained by the holding from the beading 11. By means of the movable carriages 15a, it is possible to achieve a certain transverse extension, i.e. a desired prestress of the sample 4. The sample 4 can be more easily centered, meaning that the pulling force is transmitted and distributed more effectively.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1 biaxial measuring device
2 frame
3a, 3b drives
4 sample
4a side edge
4b corner portion
5 optical measuring apparatus
6 data processing unit
7 rail
8 pulling or pushing device
9 connection device drive, pulling element
10 edge portion
11 beading
12 attachment portion
13 recess
14 beading profile block
15 a movable carriage
15b fixed carriage
16 weld seam
17 electrical connection
18 mount
19 runner rail
20 connection device/suspension device

The invention claimed is:

1. A method for determining normal stress- and shear stress-correlated material parameters using a biaxial measuring device comprising a frame for clamping a planar sample of a bendable and flexible material, a plurality of drives for applying normal and shear stresses to the sample, and an optical measuring apparatus operatively coupled to a data processing unit, the method comprising:
a) applying a predefined character grid over the planar sample, wherein an orientation of the character grid is either irregular or correlates with directions of orthotropy of the planar sample, and clamping the planar sample in the frame in accordance with the directions of orthotropy of the planar sample,
b) collecting, by the optical measuring apparatus, a first set of data that describes a first position of the character grid and sending the collected first set of data to the data processing unit,
c) applying, simultaneously, predetermined normal and shear stresses to the planar sample by the plurality of drives, thereby bringing the planar sample into a deformed state and changing the position of the character grid,
d) collecting, by the optical measuring apparatus, a second set of data that describes a second position of the character grid and sending the collected second set of data to the data processing unit,
e) determining a relative position change of the character grid by correlating the collected first set of data and the second set of data and determining therefrom, by the data processing unit, a relative displacement and a current distortion state of the planar sample,
f) determining, from the relative displacement and the current distortion state of the planar sample, a deformation equilibrium of the deformed state of the planar sample, wherein the deformation equilibrium correlates with the material parameters, and
g) calculating the material parameters from the deformation equilibrium and outputting the material parameters.

2. The method according to claim 1, wherein the normal and shear stresses simultaneously applied in step c) to deform the sample are in the non-linear range by virtue of having constantly changing tangent slopes.

3. The method according to claim 1, wherein, in order to determine the first and or second position of the character grid, distances between three predetermined points on the character grid are detected,
wherein the three predetermined points on the character grid can be joined by lines, and
wherein an angle between the lines of the points on the character grid and a predetermined x- and y-axis of the measuring device can be determined.

4. The method according to claim 1, further comprising:
g) repeatedly carrying out b) through f) while increasing or reducing the predetermined shear stress and a shear strain with each repetition.

5. A biaxial measuring device comprising:
a frame for clamping a planar sample of a bendable and flexible material, and
a plurality of drives for applying stresses to the clamped sample,
wherein the biaxial measuring device is associated with an optical measuring apparatus operatively coupled to a data processing unit,
wherein, the plurality of drives are configured to simultaneously apply predetermined normal and shear stresses to the clamped sample in normal and parallel directions with respect to directions of orthotropy of the planar sample.

6. The measuring device according to claim 5, wherein the frame is square, and
wherein the plurality of drives comprises at least eight drives, at least two of the eight drives being arranged along a side edge of the frame, at least one of the at least two drives arranged along a side edge of the frame being a first spindle drive for generating a shear stress, and at least one of the at least two drives arranged along a side edge of the frame being a second spindle drive for generating a shear strain.

7. The measuring device according to 5, wherein the plurality of drives comprises at least two drives arranged on sides of the frame that face away from one another configured to apply a uniform normal or shear stress to the sample in a predetermined direction of orthotropy.

8. The measuring device according to claim 5, wherein a rail is arranged within the frame, the rail having an edge portion mounted so as to be linearly displaceable.

9. The measuring device according to claim 5, wherein the measuring device comprises at least one control unit that is operatively connected to the data processing unit and the plurality of drives and configured to control the plurality of drives in an open- and/or closed-loop manner.

10. The measuring device according to claim 5, wherein the measuring device comprises a suspension device having a plurality of carriages configured to be connected to an edge portion of the sample.

11. The measuring device according to claim 5, further comprising a suspension device for the planar sample, the suspension device including at least three carriages that can be connected to an edge portion of the planar sample, at least two of the three carriages being movably mountable on a runner rail and at least one of the carriages being rigidly connectable to the rail.

12. The measuring device according to claim 11, wherein the suspension device further includes:

a beading around which an edge portion of the planar sample can be placed, the beading being weldable, bondable, or stitchable, to an attachment portion of the planar sample, and at least three beading, profile blocks each having a recess in which at least portions of the coverable beading can be received, the at least three beading profile blocks being connectable to the at least three carriages.

13. A measurement assembly comprising:
a biaxial measuring device including:
   a frame for clamping a planar sample of a bendable and flexible material, and
   a plurality of drives for applying stresses to the clamped sample,
   wherein the biaxial measuring device is associated with an optical measuring apparatus operatively coupled to a data processing unit,
   wherein, the plurality of drives are configured to simultaneously apply predetermined normal and shear stresses to the clamped sample in normal and parallel directions with respect to directions of orthotropy of the planar sample; and
the planar sample of a bendable and flexible material, wherein the planar sample has a planar geometry and/or comprises a character grid predefined on its surface for optically detecting distortions as a result of applicable normal and shear stresses from optically detectable points, wherein an orientation of the character grid correlates with directions of orthotropy of the planar sample.

* * * * *